United States Patent

Faccioli et al.

[11] Patent Number: 5,951,556
[45] Date of Patent: *Sep. 14, 1999

[54] COMPACT EXTERNAL FIXATION DEVICE

[75] Inventors: Giovanni Faccioli, Monzambano; Daniele Venturini, Povegliano Veronese, both of Italy; David Nelson, San Francisco, Calif.

[73] Assignee: Orthofix S.R.L., Bussolengo, Italy

[*] Notice: This patent issued on a continued prosecution application filed under 37 CFR 1.53(d), and is subject to the twenty year patent term provisions of 35 U.S.C. 154(a)(2).

[21] Appl. No.: 08/825,909

[22] Filed: Apr. 2, 1997

[30] Foreign Application Priority Data

May 15, 1996 [IT] Italy .................. VR96A00044

[51] Int. Cl.$^6$ .................................... A61B 17/60
[52] U.S. Cl. ................................. 606/65; 606/64
[58] Field of Search ............... 606/54, 55, 56, 606/57, 58, 59, 60, 72, 73

[56] References Cited

U.S. PATENT DOCUMENTS

| | | |
|---|---|---|
| Re. 31,809 | 1/1985 | Danieletto et al. . |
| 2,391,537 | 12/1945 | Anderson . |
| 4,312,336 | 1/1982 | Danieletto et al. . |
| 4,554,915 | 11/1985 | Brumfield . |
| 4,621,627 | 11/1986 | DeBastiani et al. ............ 606/54 |
| 4,643,177 | 2/1987 | Sheppard et al. ............... 606/55 |
| 4,988,349 | 1/1991 | Pennig ............................ 606/58 |
| 5,019,077 | 5/1991 | DeBastiani et al. ............ 606/54 |
| 5,292,322 | 3/1994 | Faccioli et al. . |
| 5,304,177 | 4/1994 | Pennig ............................ 606/58 |
| 5,320,622 | 6/1994 | Faccioli et al. ................ 606/58 |
| 5,342,360 | 8/1994 | Faccioli et al. . |
| 5,454,810 | 10/1995 | Pohl et al. ...................... 606/59 |
| 5,591,164 | 1/1997 | Nazre et al. .................... 606/59 |

FOREIGN PATENT DOCUMENTS

| | | |
|---|---|---|
| 0011258 | 11/1979 | European Pat. Off. ........ A61B 17/18 |
| 3722595 | 7/1987 | Germany ........................ A61B 17/60 |
| 8802463 | 5/1990 | Netherlands . |
| 8909031 | 10/1989 | WIPO . |
| 9007305 | 7/1990 | WIPO . |
| 9111150 | 8/1991 | WIPO . |
| 9111151 | 8/1991 | WIPO . |
| 9423662 | 10/1994 | WIPO . |

OTHER PUBLICATIONS

Orthofix Srl.,"Orthofix® The Pennig Dynamic Wrist Fixator, Operative Technique", Mar. 25, 1993, 47 pages.

*Primary Examiner*—Guy V. Tucker
*Attorney, Agent, or Firm*—Hopgood, Calimafde, Kalil & Judlowe

[57] ABSTRACT

A compact external fixation device for the treatment of bone fractures of reduced dimensions and of children comprises a pair of clamps (2, 3) for bone screws (V) connected by respective spherical joints (5, 6) and a central body (4) formed by at least one male element (7) and one female element (8) which are telescopically coupled. In a preferred embodiment, one element (7) is made of a material of high radiotransparency and the other element (8) is made of a substantially radiopaque rigid material with walls of such minimum thickness as to be at least partially radiotransparent. Antirotation means are provided between the male telescopic element (7) and the female telescopic element (8); transverse eccentric pins (34, 35) contained in each clamp act on respective slides (28, 29) for locking the ball (24, 25) of each joint. The fixation device permits complete radioscopy of the fracture even through the central body; the device is light in weight and of small dimensions, due to the provision of the means for locking the joints within the clamps.

33 Claims, 3 Drawing Sheets

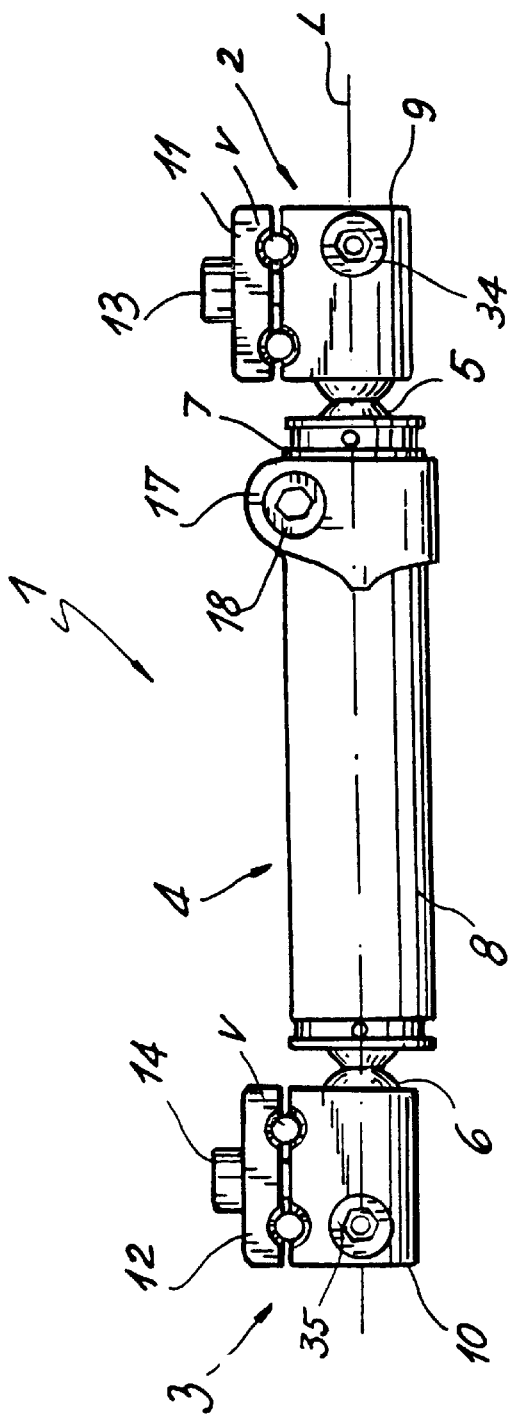
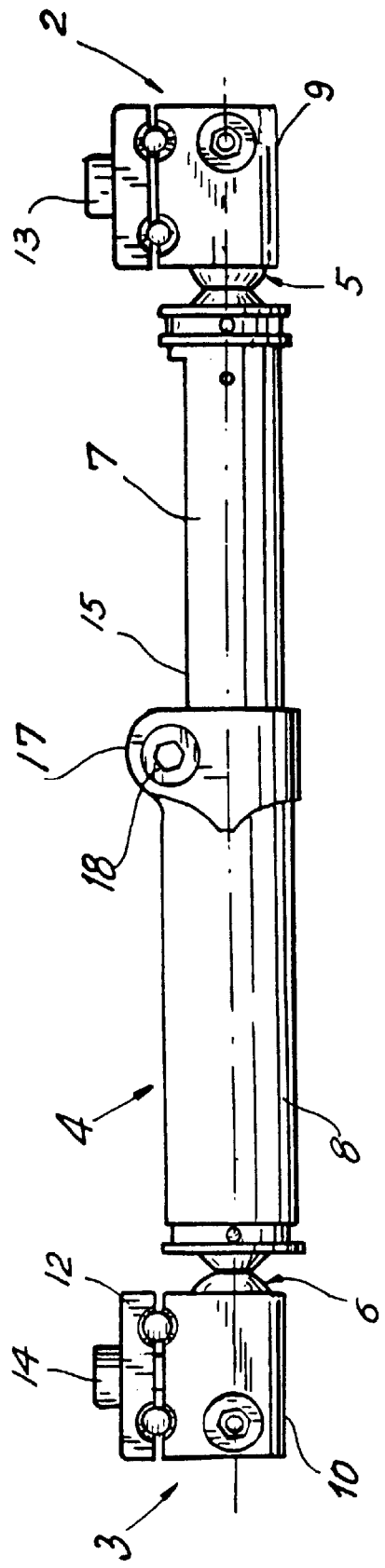
FIG. 2
FIG. 3

COMPACT EXTERNAL FIXATION DEVICE

FIELD OF INVENTION

The present invention relates to an external fixation device which is applicable in the field of bone surgery and, in particular, for the treatment of fractures in bones of reduced dimensions, such as fractures of the first metatarsus, of the wrist, of the heel and, in general, fractures of children's bones.

BACKGROUND OF THE INVENTION

Axial external fixation devices of reduced dimensions are known such as, for example, the axial external fixation device Model No. 30,000 produced and marketed by applicants' assignee and described and claimed in European Patent No. 11,258 and in U.S. Pat. No. 4,621,627.

Such known fixation devices are generally formed of an extendable central body. The longitudinal ends of the central body are connected to clamps for bone pins or screws, and each of the end connections is via a universal joint which can be releasably locked in a predetermined orientation of the clamp to the central body.

Each universal joint comprises a ball which is integral with a clamp. The rest of the joint is a socket formation at an end of the central body, and a sleeve carried by the body end captively retains the ball. An eccentric is also carried by the body end and is rotatable to selectively and releasably lock the captive orientation of the ball and thus the clamp with respect to the body. The eccentric is externally accessible for rotation by a suitable tool.

The central body is formed of two or more telescopically movable elements which can be locked in desired position by suitable locking members.

The model of the fixation device described above is produced in several sizes, one of which is intended for the reduction and stabilizing of fractures of children and of the smaller bones of adults, for example, of the wrist or ankle.

However, even this type of fixation device has several known drawbacks, among which, in particular, is the opacity of the central body to X-rays. Such opacity prevents multilateral radioscopy of fractures during a reduction and in the course of subsequent check-ups.

Another drawback of the known fixation devices resides in the large amount of space they require due to the fact that sleeves and eccentric locking devices are arranged between the central body and the respective clamps, thus accounting for an overall fixation-device length which limits the minimum distance between clamped sets of bone screws, thereby limiting the range of central-body adjustment, for a given overall fixator length.

Another drawback resides in the relatively great weight of the traditional fixation devices, particularly for the treatment of wrist fractures and in general of children and the elderly.

Another drawback of existing devices wherein the telescoping body parts are cylindrical, and therefore twistable unless locked, is that they have no means to adapt a given patient's installation to limited dynamization of the externally fixated stumps of the fracture, whereby to accelerate remarginization of the fracture.

BRIEF STATEMENT OF THE INVENTION

The principal object of the present invention is to eliminate the above-indicated drawbacks by providing an external fixation device which permits radioscopy of a fracture from any viewing point and therefore also through the fixation device.

Another object is to provide an external fixation device which is particularly compact in the longitudinal direction so as to be suitable for the treatment of fractures of the small bones of adults and, in general, of the bones of children.

Still another object is to provide a fixation device which is of substantially less weight.

A further object is to provide a fixation device meeting the above objects and also offering reliable torsional stiffness between end-locked orientations of the respective joints.

The invention in its preferred embodiment achieves these and other objects in an external fixation device wherein separate bone-screw clamps are connected to the respective longitudinal ends of an extendable central body, via releasably lockage ball joints, wherein the central body is formed of two telescopic tubular elements which are at least partially radiotransparent.

Preferably, at least one of the telescopic elements is made of a material of high transparency to X-rays while the other is made of a substantially radiopaque material but with side walls of such thickness as to provide mechanical strength and at least partial radiotransparency.

In this way, it will be possible to examine the fracture by X-ray from all viewing points, including through the central body of the fixation device, which therefore will no longer constitute an impediment or a limitation for the inspection of the fracture.

BRIEF DESCRIPTION OF THE DRAWINGS

The invention will be illustratively described in detail in conjunction with the accompanying drawings, in which:

FIG. 2 is a side view of the fixation device of FIG. 1, in fully retracted condition;

FIG. 3 is another side view of the fixation device of FIG. 1 in fully extended condition;

DETAILED DESCRIPTION

Figures 1, 10:
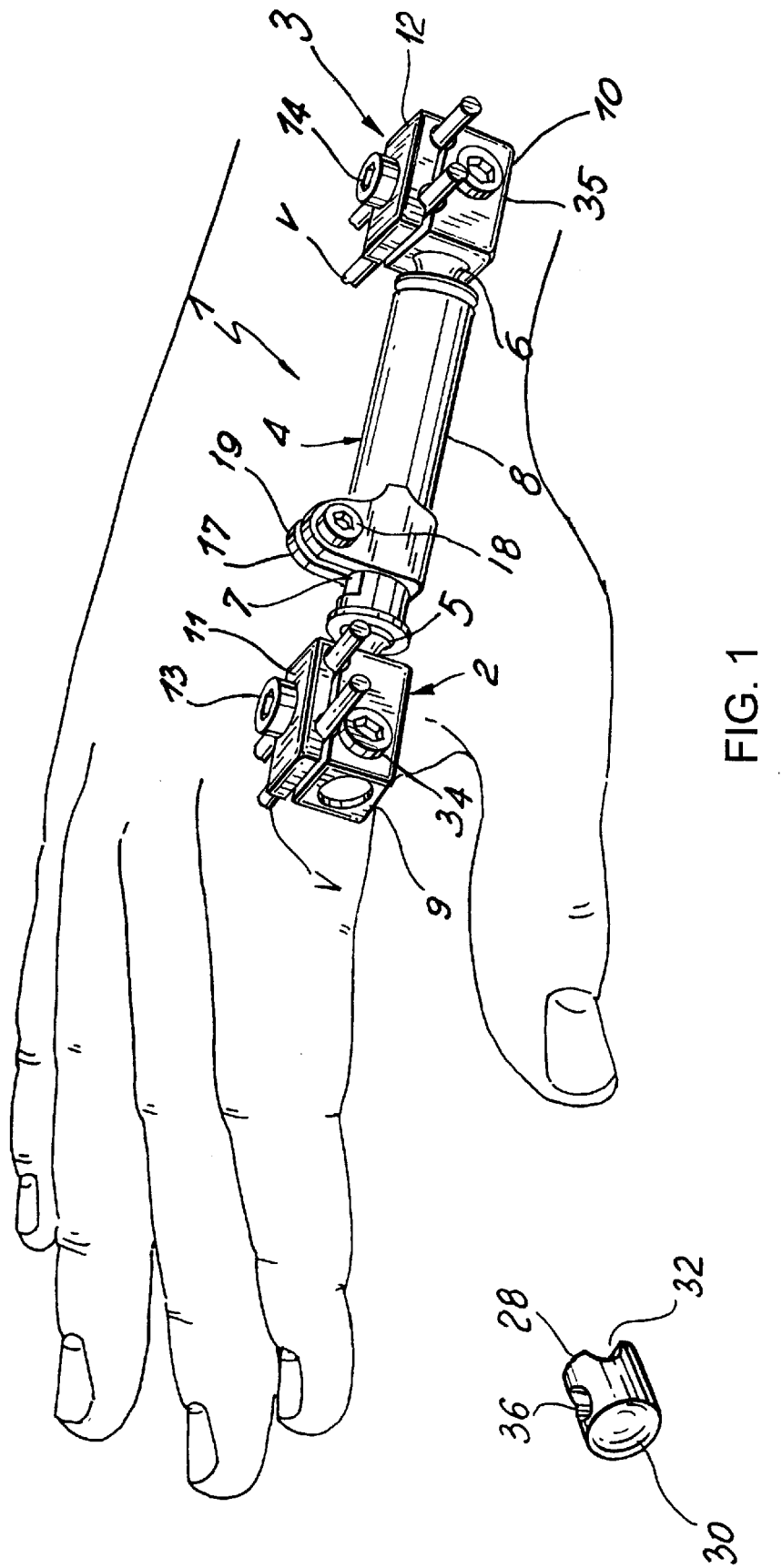
FIG. 1 is an overall view in perspective, for an external fixation device of the invention, installed near a patient's wrist joint, and in partially expanded condition.
FIG. 10 is a perspective view of one of the parts of releasably lockable connection of the clamp of FIG. 9 to the central-body part of FIG. 9.

In the drawings, an external axial-fixation device of the invention is indicated generally by reference numeral 1.

The device comprises a pair of clamps 2, 3 for clamping bone screws or pins V that have previously been surgically inserted in stumps of a fracture, for example, of a wrist joint. The clamps 2, 3 are attached by end joints 5, 6 to the respective longitudinal ends of an extendable central body 4.

The central body 4 can be formed of two elements, a male or inner element 7 and a female or outer element 8, of approximately cylindrical shape and circular cross section; the elements 7, 8 are telescopically related so that they can slide one within the other along a common longitudinal axis L, thereby varying the total length of the central body 4.

The clamps 2, 3 are preferably formed of main body portions 9, 10 respectively, of approximately prismatic or parallelopiped shape, connected to corresponding clamp plates 11, 12 by screws 13, 14, for clamped engagement to the bone pins V.

In accordance with a feature of the invention, the telescopic elements 7, 8 are at least partially radiotransparent in order to permit radioscopy of the fracture through the central body 4.

Preferably, at least one of the telescopic elements, in particular the male or inner element 7, is made of a material of high radiotransparency.

The material of high radiotransparency may be a thermoplastic resin of amorphous or semicrystalline structure, selected from among the polyethers, polysulfonates, polyoxymethylenes and polyetherimides.

The female or outer telescopic element 8 is preferably made of a substantially radiopaque material, for example, an aluminum alloy, and has side walls of such slight thickness as to be at least partially radiotransparent, while also providing adequate mechanical strength.

From calculations and tests, it has been verified that by making a female (outer) telescopic element 8 with side walls of thickness S not greater than about 1 mm, sufficient strength and radiotransparency are obtained for the central body as a whole.

In order to obviate the problem of relative rotation of the telescopic elements 7, 8 and therefore of the bone-screw clamps 2, 3 in the dynamiting phase of the fixation device, suitable anti-rotation blocking means are provided.

In particular, the male (inner) telescopic element 7 has an elongate flat 15 which extends over almost its entire length while leaving a projecting lip 16 at its distal end.

Figure 5:
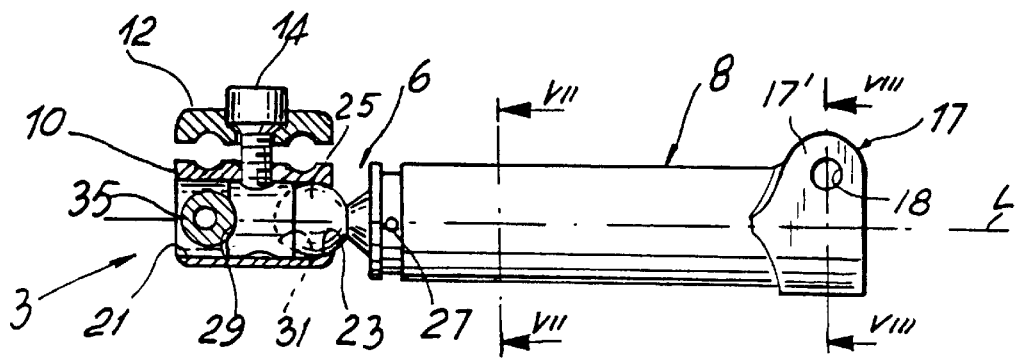
FIG. 5 is a similar side view of the other of said central body parts, with end detail in partial longitudinal section for another bone-screw clamp connected to the opposite end of said other part.
Figure 6:
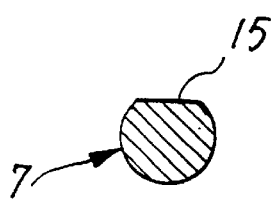
FIG. 6 is a cross section, taken at VI—VI of FIG. 4.
Figure 7:
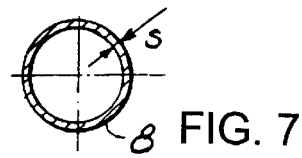
FIG. 7 is a cross section, taken at VII—VII of FIG. 5.
Figure 8:
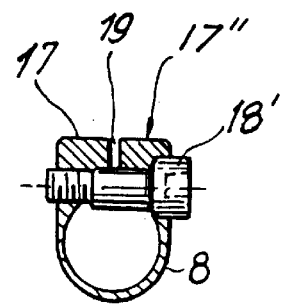
FIG. 8 is a cross section, taken at VIII—VIII of FIG. 5.

The female element 8 has, at its distal or free end, longitudinally opposite the clamp 3, a local laterally outward projection or ear 17, which has a cut slit 19 in a radial plane that extends longitudinally at least for the longitudinal dimension of projection 17, thereby defining two confronting ear formations 17', 17" at a locally slit distal-end region of the outer body part 8, as best seen in FIG. 8. A transverse bore 18 (FIG. 5) through the ear formations 17', 17" is seen in FIG. 8 to provide threaded engagement to ear formation 17' for the distal end of a bolt 18', while the head end of bolt 18" is seated in a suitable counterbore in the other ear formation 17"; and a smoothly cylindrical shank portion of bolt 18' (between the head and threaded ends of bolt 18') will be seen to intrude into the local cylindrical section of the bore of the outer-body part 8 for a key-like relation to the flat 15 of the inner-body part 7, so as to prevent relative rotation of the body parts 7, 8 about the longitudinal axis L, whatever their extended or contracted telescopic relation.

The slit or cut 19 will be understood to be of sufficient axial extent to provide a degree of local radial or circumferential resilience at the distal end of the outer-body part 8. The bolt 18' which engages ear formation 17', via ear formation 17", can therefore clamp the end of the outer element 8, locking the inner element 7 in a desired position. Furthermore, bolt 18' will be seen to provide a stop at interfering abutment with lip 16, thus preventing a unintended separation of body parts 7, 8 from each other.

Figure 9:
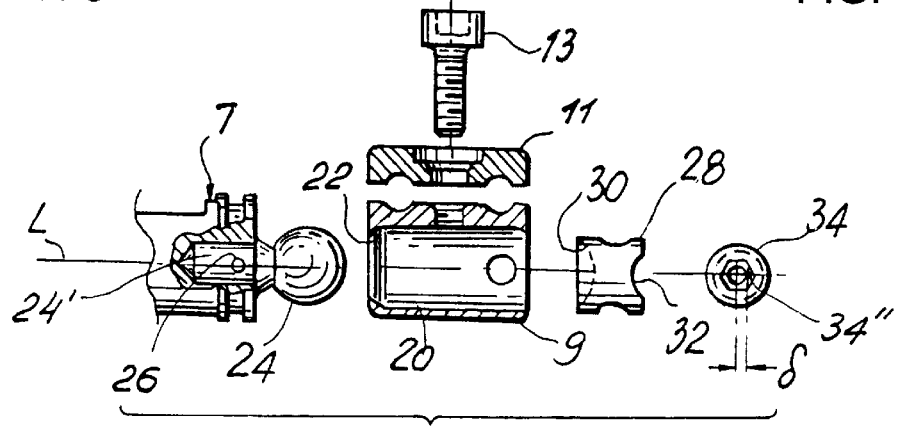
FIG. 9 is a fragmentary exploded view, and in partial section, through one of the bone-screw clamps and its connection to one of the central-body parts of the device of FIGS. 1 to 3.

It can be noted that the main prismatic or body portions 9, 10 of each of the clamps 2, 3 have continuous cylindrical cavities 20, 21, each with its own inwardly formed spherical restriction or lip 22, 23 for engaged-ball retention. As shown, illustratively for the ball 24 of FIG. 9, (i) the ball diameter should have running clearance with the bore 20 and should exceed the inner diameter of the inward lip formation 22, (ii) the ball 24 is preferably of one piece, with its mounting stem 24' pinned at 26 to the proximal end of inner-body part 7, and (iii) the truncated frustoconical base, which provides a circumferentially continuous radial shoulder for abutment reference to the flat end surface of part 7, should be of outer diameter (less than ball diameter) that is sized to enable its assembling passage through the inward lip 22 at the end of the bore 20. In the drawings, the bore 20, lip 22, and the stem 24' for mounting ball 24—all for ball-joint connection to inner-body part 7—will be understood to have corresponding features at bore 21, lip 23, and ball 25 (with its stem 25') for ball-joint connection to outer-body part 8.

Figure 4:
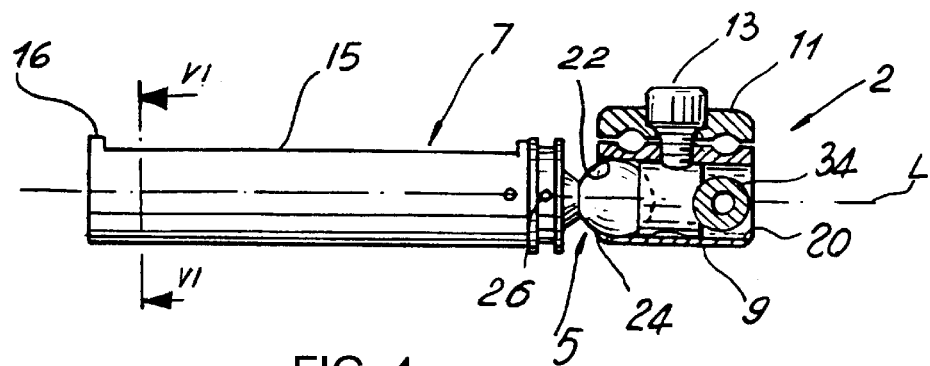
FIG. 4 is a side view of the inner one of two telescopically related central-body parts of the device of FIGS. 1 to 3, with end detail in partial longitudinal section for a bone-screw clamp connected to one end of said inner part.

Each of the cylindrical cavities 20, 21 accommodates a thrust slide (28, 29) having an outer cylindrical surface, of diameter to establish an axially guided running fit to the bore diameter of the cavity (20, 21), within which it is captive. A first end (30, 31) of each thrust slide (28, 29) is spherically concave for ball-seating engagement, and a second end (32, 33) of each thrust bushing is cylindrically concave on a diametrically extending axis that is normal to the longitudinal axis of its guidance cavity (20, 21). Finally, closure of each cavity is completed by a transverse pin or rotary cam (34, 35) having an eccentric portion for engagement with the cylindrically concave end of its adjacent bushing. The journalling of transverse pin 34 in clamp body 9 will be understood from the transverse-journalling bore 34' in FIG. 9, and the eccentric throw δ of the body of pin 34 will be understood from the schematic designation 34" shown in FIG. 9 for pin 34. As shown, a simple rotary manipulation of an Allen-head wrench to pin 34 (in FIG. 4) serves for selective eccentrically driven displacement of its associated thrust slide into releasably locked retention of ball 24, for any given orientation of clamp 9 with respect to the longitudinal axis of the central body part 7 to which it is connected.

The described arrangement of the eccentrics (34, 35) on the clamp bodies (9, 10), in particular toward their distal ends, and utilizing body structure (9, 10) of the respective bone-screw clamps (2, 3) will be seen to have effected an overall reduction in longitudinal size of the fixation device as a whole. Thus, the minimum distance between the clamps (2, 3), and therefore between bone screws V driven into bone on opposite sides of a fracture, is less than heretofore, permitting optimal use of the fixation device in a wrist-joint situation and, in general, for small bones and for bones of children.

Use of the described fixation device can be seen from the foregoing description, but an illustrative case will be briefly described.

Having first set multiple screws V in the respective stumps of a fractional bone, all clamp screws (13, 14) and 18, and eccentrics 34, 35 are first backed off from a previously clamped relation, to permit complete freedom for bone-screw clamping, length adjustment and ball-joint orientation. Whereupon, the length of the central body is adjusted to permit insertion of bone screws V between plates 11, 12 and the clamp-body portions 9, 10 of the respective clamps (2, 3). Clamp bolts 13, 14 are first tightened via their threaded engagement to their respective body structures (9, 10), and then the eccentrics 34, 35 are tightened to lock the ball-joint orientations and therefore to lock the orientation of the clamps (2, 3) with respect to the central body parts (7, 8); as seen in FIG. 10, a diametrically extending, longitudinally central bore 36 in each thrust slide is sized for sufficient clearance with possible bolt (13) thread entry, without impairing the described eccentric-driven displacement involved in releasably clamped ball engagement. Finally, bolt 18' is tightened to fix the length of the central body.

Due to the radiotransparency of the central body, it is possible to carry out the entire operation of reduction of a fracture while exposing the fracture to X-rays. Also, operation and use of the described fixator is simplified, with greater facility for maneuvering and reduction of the times of personnel exposure to X-radiation.

The fixation device of the invention is capable to numerous modifications and variants which fall within the scope of the accompanying claims. And the dimensions, shapes and materials may also be modified without departure from the scope of the invention.

What is claimed is:

1. A compact external fixation device, suitable for the treatment of fractures of bones of reduced dimensions and of children, comprising a pair of clamps (2, 3) for bone screws (V) connected by respective lockable ball joints (5, 6) to a central body (4) of adjustable length formed of at least one male element (7) and one female element (8), which elements can be coupled telescopically, wherein the male element (7) is of a material of high radiotransparency and wherein the female element (8) is a sleeve of substantially radiopaque rigid material with wall structure of such small thickness (S) as to be at least partially radiotransparent.

2. An external fixation device according to claim 1, in which said material of high radiotransparency is a thermoplastic resin or an amorphous or semicrystalline structure.

3. An external fixation device according to claim 2, in which said thermoplastic resin is selected from the group consisting of polyesters, polysulfonates, polyoxymethylenes and polyetheramides.

4. An external fixation device according to claim 1, in which said substantially radiopaque material is a metallic alloy having a base of aluminum.

5. An external fixation device according to claim 4, in which the wall of said female element (8) of radiopaque material has a thickness at most equal to about 1 mm.

6. A compact external fixation device, suitable for the treatment of fractures of bones of reduced dimensions and of children, comprising a pair of clamps (2, 3) for bone screws (V) connected by respective lockable ball joints (5, 6) to a central body (4) of adjustable length formed of at least one male element (7) and one female element (8), which elements can be coupled telescopically, wherein said telescopic elements (7, 8) are at least partially radiotransparent so as to permit radioscopy of the fracture even through the central body (4); each clamp (2, 3) comprising a substantially prismatic portion (9, 10) having a continuous axial cavity (20, 21) in which there is housed a ball (24, 25) connected to a respective telescopic element (7, 8); a stop sleeve (28, 29) inserted in a respective continuous axial cavity (20, 21), said sleeve (28, 29) having at one longitudinal end a first substantially semispherical seat 30, 31 adapted to interact with a respective ball (24, 25) and at the opposite longitudinal end a diametral cylindrical seat (32, 33); and a transverse eccentric pin (34, 35) rotatably supported at the free end of each clamp (2, 3) so as to interact with a respective bushing (28, 29) in correspondence with the diametral seat (32, 33) of the latter and to lock said ball (24, 25).

7. An external fixator, comprising an elongate central body with first and second bone-screw clamps ball-joint-connected to the respective longitudinal ends of said body;

said body comprising an elongate outer-body member having a cylindrical bore with a distally open end and a closed proximal end adapted for ball-joint connection to one of said bone-screw clamps, and an elongate inner-body member having a cylindrical body portion telescopically guided by said cylindrical bore, said inner-body member having (i) a distal end received in said bore via the distally open end of said outer-body member and (ii) a proximal end adapted for ball-joint connection to the other of said bone-screw clamps;

said inner-body member having an angularly local chordal flat extending longitudinally between but short of the proximal and distal ends of said inner-body member;

the distal end of said outer-body member having an angularly local, axially extending slit of limited axial extent, thereby defining angularly spaced confronting relatively compliant clamp elements, said clamp elements having aligned bores on a transverse axis through said clamp elements and at radial offset from the axis of said cylindrical bore; and bolt means engaged to both of said clamp elements on said transverse axis for releasably clamping said elements to retain a telescopically adjusted central-body length between said bone-screw clamps, at least a portion of said bolt means chordally traversing the geometrical volume within and between said clamping elements to establish an anti-rotational relation between said inner and outer body members.

8. The external fixator of claim 7, wherein said bolt means comprises an elongate bolt with a smoothly cylindrical shank portion between an enlarged head at one end and a threaded portion at its other end, one of said aligned bores being sized to receive and locate said shank portion, the other of said aligned bores being tapped for threaded reception of the threaded end of said bolt.

9. The external fixator of claim 8, wherein the clamp element having the bore which is sized to receive and locate said shank portion is externally counterbored to provide a seat for said enlarged head.

10. The external fixator of claim 8, wherein the diameter of said shank portion is sized for running clearance with the chordal flat of said inner-body member.

11. The external fixator of claim 7, wherein each of the ball-joint connections to the respective bone-screw clamps comprises a ball element with an integrally formed mount fixedly secured to the proximal end of the body member with which it is associated.

12. The external fixator of claim 11, in which the mount for each ball element comprises a frusto-conical base, and a reduced cylindrical projection on an axis in common with the conical axis of said base and with the ball center.

13. The external fixator of claim 7, wherein each ball-joint connection comprises a ball element carried by the proximal end of one of central-body members, and wherein each bone-screw clamp includes (i) a socket formation for a ball element and (ii) selectively operable means carried by each bone-screw clamp, for releasably clamping a selected orientation of the applicable ball-joint connection.

14. The fixator of claim 13, wherein said socket formation comprises a clamp-body member having an elongate clamp bore which is sized for running clearance with a ball element and which has a ball-retaining inward lip formation at a ball-retaining end of the clamp bore, a cam-follower slide axially guided by the clamp bore and having a concave-spherical surface at one axial end for ball engagement and a diametrically extending concave-cylindrical surface at its opposite axial end for cam-following engagement, and rotary-cam means journalled in a transverse bore of said clamp-body member for releasably driving the ball element via said slide and into locking engagement with said retaining lip.

15. The external fixator of claim 13, wherein each bone-screw clamp comprises a generally rectangular-prismatic body with a first flat clamping surface, a clamping plate with a second flat surface overlapping said first flat surface, there being at least two spaced bone-screw locating grooves on at least one of said surfaces, and a bolt through said plate for securing bone screws to said prismatic body, said prismatic body having an elongate clamp bore sized for running clearance with a ball element, a ball-retaining inward lip formation at a ball-retaining end of said clamp bore, and means including a rotary cam journalled in a transverse bore of said prismatic body for releasably driving the ball element into locked engagement with said lip formation.

16. The external fixator of claim 15, wherein said clamp bore is on an axis parallel to said first flat surface.

17. The external fixator of claim 15, wherein a slide element is axially guided by said clamp bore and is interposed between said rotary cam and the ball for cam-following transfer of cam thrust in the direction of locking the ball to said retaining lip formation, said slide element having a diametrically extending bore between its cam-following and ball-engaging axial ends, the diametrically extending bore being generally aligned with said bolt but in radial clearance therewith, whereby said bolt may provide a loosely retained axially central location of said slide without impairing a cam-actuated lock of ball orientation.

18. The external fixator of claim 7, in which said inner-body member is of radio-transparent material, and the outer-body member is cylindrical and of such relatively thin-wall metal as to be partially radiotransparent and thus to permit viewing of a fracture via radioscopy through the thin-wall metal.

19. The external fixator of claim 18, in which said metal is an aluminum alloy.

20. The external fixator of claim 7 wherein at least one of said inner- and outer-body members is of radio-transparent material.

21. An external fixator comprising an adjustably extendable elongate body with first and second bone-screw clamps ball-joint-connected to the respective longitudinal ends of said body, each of said longitudinal ends having an affixed ball element extending outward for socket reception at the bone-screw clamp to which it is thus connected, and each bone-screw clamp comprising:

a rectangular-prismatic body with a first flat clamping surface, a clamping plate with a second flat surface overlapping said first flat surface, at least two bone-screw locating grooves on one of said surfaces, and a bolt through said plate and engaged to said prismatic body for securing bone screws to said prismatic body, said prismatic body having an elongate clamp bore sized for running clearance with a ball element and having a ball-retaining inward lip formation at a ball-retaining end of said clamp bore, and means including a rotary cam journalled in a transverse bore of said prismatic body for releasably driving the ball element into locked engagement with said lip formation.

22. The external fixator of claim 21, whereby said clamp bore is on an axis parallel to said first flat surface.

23. The external fixator of claim 21, wherein a cam-follower slide is axially guided by the clamp bore, said slide having a concave-spherical surface at one axial end for ball engagement and a diametrically extending concave-cylindrical surface at its opposite axial end for cam-following engagement with said cam formation, said rotary cam means journalled in a transverse bore of said prismatic body for releasably driving the ball element via said slide and into locking engagement with said retaining lip.

24. The external fixator of claim 21, in which the material of said extendable body is at least partially radiotransparent.

25. An external fixator, comprising an elongate central body with first and second bone-screw clamps connected to the respective longitudinal ends of said body, said body comprising an elongate outer-body member having a cylindrical bore with a distally open end and a closed proximal end adapted for connection to one of said bone-screw clamps, and an elongate inner-body member having a cylindrical body portion telescopically guided by said cylindrical bore, said outer body member being of radiopaque material, said inner-body member having (i) a distal end received in said bore via the distally open end of said outer-body member and (ii) a proximal end adapted for connection to the other of said bone-screw clamps, said inner-body member being of radio-transparent material.

26. The external fixator of claim 25 wherein at least one of said bone-screw clamps is ball-joint-connected to the respective longitudinal end of said body.

27. The external fixator of claim 26 wherein both of said bone-screw clamps are ball-joint-connected to the respective longitudinal ends of said body.

28. The external fixator of claim 25, wherein said radio-transparent material is a thermoplastic resin of an amorphous or semicrystalline structure.

29. The external fixator of claim 28, wherein said thermoplastic resin is selected from the group consisting of polyesters, polyethers, polysulfonates, polyoxymethylenes, polyetherimides and polyetheramides.

30. The external fixator of claim 25, wherein said outer body member is of radiopaque material.

31. The external fixator of claim 30, wherein said outer body member is of an aluminum alloy.

32. The external fixator of claim 30, wherein said outer body member is cylindrical, said radiopaque material being defined by sufficiently thin-walled metal of said cylindrical outer body member.

33. The external fixator of claim 32, wherein the maximum radial thickness of said cylindrical wall of said outer body member is 1 mm.

\* \* \* \* \*